United States Patent [19]

Burns

[11] Patent Number: 4,941,880
[45] Date of Patent: Jul. 17, 1990

[54] PRE-FILLED AMPULE AND NON-INVASIVE HYPODERMIC INJECTION DEVICE ASSEMBLY

[75] Inventor: Marvin Burns, Marina Del Rey, Calif.

[73] Assignee: Bioject, Inc., Portland, Oreg.

[21] Appl. No.: 284,063

[22] Filed: Dec. 12, 1988

Related U.S. Application Data

[63] Continuation-in-part of Ser. No. 64,762, Jun. 19, 1987, Pat. No. 4,790,824.

[51] Int. Cl.$^5$ ............................................. A61M 37/00
[52] U.S. Cl. ..................................... 604/143; 604/68; 604/70
[58] Field of Search ............... 604/232, 143, 142, 218, 604/130, 131, 134, 68, 69, 70

[56] References Cited

U.S. PATENT DOCUMENTS

| | | |
|---|---|---|
| 2,547,099 | 4/1951 | Smooth . |
| 2,704,543 | 3/1955 | Scherer . |
| 2,737,946 | 3/1956 | Hein, Jr. . |
| 2,764,977 | 10/1956 | Ferguson . |
| 3,688,765 | 9/1972 | Gasaway . |
| 3,695,266 | 10/1972 | Lussier . |
| 3,853,125 | 12/1974 | Clark et al. . |
| 3,945,379 | 3/1976 | Pritz et al. . |
| 3,945,383 | 3/1976 | Bennett et al. . |
| 4,403,989 | 9/1983 | Christensen et al. . |
| 4,596,556 | 6/1986 | Morrow et al. . |
| 4,680,027 | 7/1987 | Parsons et al. . |
| 4,717,384 | 1/1988 | Waldeisen .......................... 604/143 |
| 4,790,824 | 12/1988 | Burns ................................. 604/143 |

FOREIGN PATENT DOCUMENTS 492587  5/1953  Canada .

Primary Examiner—John D. Yasko
Attorney, Agent, or Firm—Lyon & Lyon

[57] ABSTRACT

A pre-filled ampule and a powered, non-invasive injection device assembly wherein the device includes a housing having an ampule-receiving chamber, a gas charge, and means for delivering a predetermined amount of gas to an ampule-receiving chamber. The device includes an injection-counting ring which is received in a groove extending about the housing wherein the ring includes a counting mechanism thereon and is constructed to allow one-way only rotation thereof relative to the housing. The ampule includes an elongate ampule body having a medication holder located at one end thereof, a transfer area located adjacent the other end thereof and a bypass area located adjacent an end of the transfer area. A plunger is provided and has one end thereof received in and closing one end of the medication holder with the other end of the plunger being received in the ampule-receiving chamber of the injection device. A floating seal is received and encloses the other end of the medication holder. Orifice means are provided for forming a skin-piercing injection stream. Attachment means are provided for securing the ampule to the device.

15 Claims, 2 Drawing Sheets

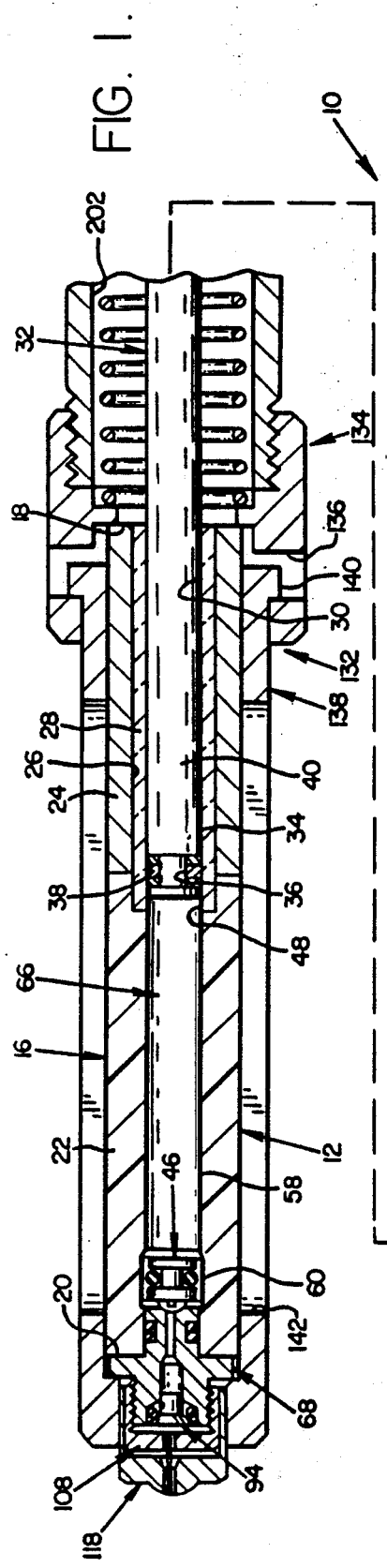

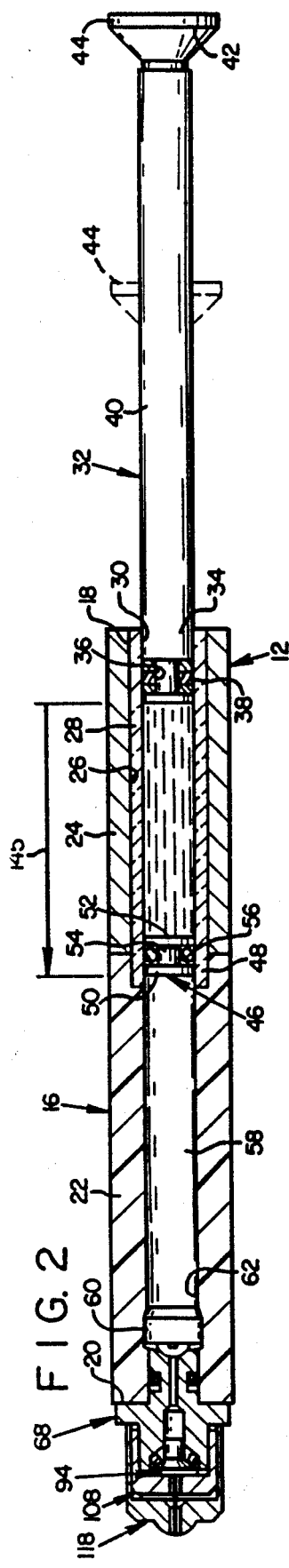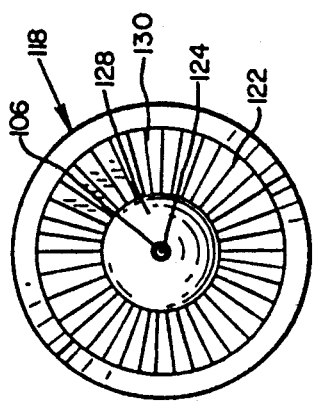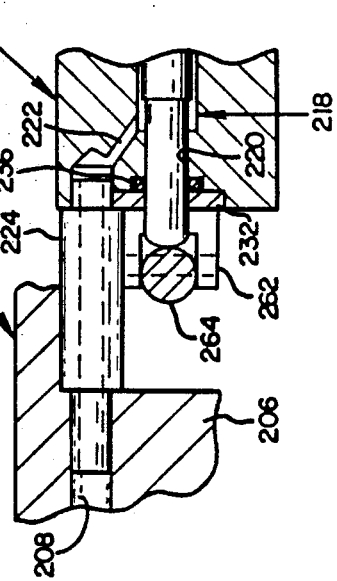

PRE-FILLED AMPULE AND NON-INVASIVE HYPODERMIC INJECTION DEVICE ASSEMBLY

This is a continuation-in-part of U.S. patent application Ser. No. 064,762, filed June 19, 1987 for NONINVASIVE HYPODERMIC INJECTION DEVICE, now U.S. Pat. No. 4,790,824. A co-pending U.S. patent application Ser. No. 283,737 was filed on Dec. 12, 1988 for A PATIENT-FILLABLE AMPULE AND NON-INVASIVE HYPODERMIC INJECTION DEVICE ASSEMBLY.

BACKGROUND OF THE INVENTION

The invention relates to medication injecting device assemblies and specifically to a pre-filled ampule for use with a hypodermic injection device which injects medication but which does not require piercing the skin of a patient with a hypodermic needle.

The medication ampules used with powered hypodermic devices are generally formed of high-strength plastic material which are capable of withstanding the pressures, generally in the vicinity of 8000 psi, which are utilized to inject medication through the skin of a patient without piercing the skin of the patient with a hypodermic needle. The ampules, or syringes, have sidewalls which are considerably heavier than those of conventional syringes and are usually formed of a plastomer material. A problem with the use of such plastics, such as polycarbonate, is that the plastic will react with, or diffuse into, the medication which is to be administered should the medication be present in the ampule for an extended period of time. This is particularly important in the case where it is desired to provide a patient with a pre-filled ampule which contains a precise measurement of medication. Such an ampule must be capable of being stored with the medication contained therein for an extended period of time yet must not contaminate the stored medication.

Injectable medication is usually stored in glass containers because glass is generally inert with respect to injectable medications and will not contaminate the stored medication stored therein. The provision of a glass ampule would therefore eliminate the problem of contamination if the medication is stored within the ampule for an extended period of time. However, a glass ampule would be required to have an unreasonably thick sidewall in order to withstand the pressures imparted thereto by the powered hypodermic device which is used in conjunction with the ampule.

Powered hypodermic devices are known which provide one or more gas charges to deliver injections by non-invasive hypodermic means. Generally, the smaller powered hypodermic devices, which are intended for use by patient self-administered medication, are one-shot devices in that a new gas charge containing cartridge must be provided for each injection. Larger devices are known which provide multiple injections from a single gas charge, but these devices are generally quite large and too expensive for patient-administration of medication. It is particularly important that patients who self-administer medication know how many times the device has been used on a given charge, so that the patient will not attempt to administer medication when the device does not have sufficient gas charge therein to provide a complete injection of the medication.

An object of the instant invention is to provide a pre-filled ampule for a powered-hypodermic injection device which will provide extended storage of medication therein without contamination of the medication by the material from which the ampule is formed.

Another object of the instant invention is to provide a medication holder formed of inert material which is capable of sustaining the high pressures imparted by a powered hypodermic injection device.

A further object of the invention is to provide a pre-filled ampule which may be filled with a precise, known amount of medication by a medication manufacturer.

Still another object of the invention is to provide a powered hypodermic injection device which is capable of providing multiple injections.

Another object of the invention is to provide such a device which includes means for indicating the number of injections administered on a particular gas charge.

SUMMARY OF THE INVENTION

The invention includes an injection device which includes a housing having an ampule-receiving chamber, a gas charge, and means for delivering a predetermined amount of gas to the ampule-receiving chamber. The device includes an injection-counting ring which is received in a groove extending about the housing wherein the ring includes a counting mechanism thereon and is constructed to allow one-way only rotation thereof relative to the housing. The pre-filled ampule includes an elongate, cylindrical ampule body having an inert medication holder located at one end thereof, a transfer area located adjacent the other end of the body and a bypass area located adjacent an end of the transfer area. A plunger is provided and has one end thereof received in and closing one end of the medication holder with the other end of the plunger being received in the ampule-receiving chamber of the injection device. A floating seal is received and closes the other end of the medication holder. Orifice means are provided for forming a skin-piercing injection stream. Attachment means are provided for securing the ampule to the device.

These and other objects and advantages of the invention will become more fully apparent as the description which follows is read in conjunction with the drawings.

BRIEF DESCRIPTION OF THE DRAWINGS

FIG. 1 is a medial section of the invention, with the ampule depicted in a ready condition.

FIG. 2 is a medial section of the ampule of the invention shown in an initial condition.

FIG. 3 is a medial section of the ampule shown in a spent condition.

FIG. 4 is a greatly enlarged medial section of the orifice end of the ampule.

FIG. 5 is a greatly enlarged end view of a needle standoff of the invention, taken generally along the line 5—5 of FIG. 4.

FIG. 6 is an exploded perspective view of attachment means of the invention.

FIG. 7 is an enlarged section of an actuator mechanism of the invention.

FIG. 8 is a cross section of one end of a valve assembly of the invention, taken generally along the line 8—8 of FIG. 1.

DETAILED DESCRIPTION OF THE PREFERRED EMBODIMENT

Referring now to the drawings, and initially to FIG. 1, an ampule and a non-invasive hypodermic injection device assembly constructed according to the invention is shown generally at 10. Assembly 10 includes a prefilled, medication-containing ampule, indicated generally at 12, and a powered hypodermic injection device, indicated generally at 14.

Referring now to FIGS. 1 and 2, ampule 12 includes an elongate, cylindrical ampule body 16 which has a plunger end 18 and an orifice end 20. In the preferred embodiment, body 16 is formed from two separately molded portions 22, 24, of polycarbonate material. This material is capable of withstanding an internal pressure of at least 8000 psi, which is to be expected when a gas charge contained in device 14 is used to form a skin-piercing injection stream from ampule 12. Portions 22, 24 may be formed by any suitable manufacturing process, such as injection molding, machining, or a combination thereof. The two portions may be joined together by suitable adhesive or joining technique such as ultrasonic welding.

Portion 24 includes a medication holder-retaining area 26 therein which receives a medication holder 28. Holder 28 is an elongate, generally cylindrical element which is formed from a non-absorbing, non-diffusing, non-reacting material and is received in the medication holder-retaining area and secured thereto by adhesive or welding. In the preferred embodiment, holder 28 is formed of glass, although in some instances, a metal medication holder may be used so long as the metal is essentially non-reactive with the medication received therein. Holder 28 is strengthened or bolstered by surrounding portion 24 to withstand assembly pressures. Holder 28 includes a free, plunger-receiving end 30 which, in the preferred embodiment, is co-terminally located with plunger end 18 of body 16.

A plunger 32 has one end 34 thereof received in plunger-receiving end 30 of medication holder 28. Plunger one end 34 includes a groove 36 formed adjacent the end thereof and a seal 38 located in the groove. The plunger is therefore operable to close one end of medication holder 28 when the ampule is in the initial condition, as depicted in FIG. 2. Plunger 32 includes a shaft 40 which extends between one end 34 and the other end 42 thereof. Other end 42 includes an enlarged head 44 which is received in device 14.

Referring now to FIG. 2, a floating seal 46 is depicted at the interior, other, end 48 of medication holder 28. In the preferred embodiment, seal 46 includes a machined or molded groove 56 defined between surfaces 50, 52 and surrounding a core 54, to accommodate an O-ring seal. An O-ring 56 is received on core 54. Seal 46 is received in the other end of medication holder 28 and closes the other end.

A transfer area 58 is located in portion 22 adjacent orifice end 20 of body 16. A bypass area 60 is located at one end 62 of transfer area 58 adjacent the orifice end 20 of body 16. In the preferred embodiment, bypass area 60 includes an enlarged region with four key ways 64 spaced thereabout. Bypass area 60 is sized to allow floating seal 46 to lodge therein while medication 66 is moved from transfer area 58 through an orifice.

Referring now to FIG. 4, the components located adjacent orifice end 20 of body 16 will be described. An ampule end bushing 68 is received on the free end of portion 22. Bushing 68 has a generally disc-like portion 70 and extensions 72, 74 protruding from either side thereof. Extension 72 is sized to be received in transfer area 58 and includes a groove 76 extending thereabout. In the preferred embodiment, an O-ring 78 and a backup seal 80 are received in groove 76 to provide a high-pressure withstanding seal between the end bushing and portion 22. Extension 74 extends axially outward from disc portion 70 and has a threaded periphery 82 formed thereon. A channel 84 extends through bushing 68. Channel 84 includes a depressed area 86 having a generally spherical form, which connects to a first channel segment 88, which is in turn connected to a second, expanded channel segment 90. The other end of channel 84 includes a further expanded region, or orifice receiver, 92. In the preferred embodiment, ampule end bushing 68 is formed of machined aluminum alloy.

A needle orifice holder 94 is positioned in orifice receiver 92. Holder 94 includes a ferrule 96 and a truncated hypodermic needle 98 which is secured therein. A channel 100 extends through ferrule 96 and is continuous with a channel 102 in needle 98. Holder 94 is sealed to bushing 68 by means of an O-ring 104. In the preferred embodiment, needle 98 is formed from stainless steel and has a flat, or slightly tapered, free end, 106.

Holder 94 is retained in bushing 68 by an orifice end cap 108. End cap 108 has threads 110 formed on the interior of a side 112 thereof which are conformal with threads 82 of bushing 68. An end 114 of end cap 108 has a bore 116 therethrough which allows passage of needle 98. End bushing 68, holder 94 and end cap 108 comprise what is referred to herein as orifice means.

A needle standoff 118, and now referring to FIGS. 4 and 5, is provided to prevent penetration of the skin of an injection-receiving patient by needle 98. In the preferred embodiment, standoff 118 is a substantially cylindrical object having a sidewall 120 which extends over end cap 108. The end 122 of the standoff is configured with a bore 124 extending therethrough to receive needle 98. Bore 124 has a flared portion 126 at the interior end thereof. A raised area 128 is located around bore 124 and provides a depressed area on the patient's skin when the assembly is brought in contact therewith. A slip-inhibiting surface 130 is formed about raised area 128 to increase traction between the assembly and the patient receiving the injection.

Referring now to FIGS. 1 and 7, attachment means for attaching ampule 12 to device 14 are shown generally at 132. In the preferred embodiment, attachment means includes a retaining collar 134 which is secured to device 14. Retaining collar 134 is secured to device 14 in the preferred embodiment by means of threads on the device and on the collar. Collar 134 also has lug-receiving grooves 136 formed thereon.

Attachment means also includes an elongate ampule sleeve 138 which extends about the ampule body along the length thereof and which has a series of lugs 140 arranged about the periphery of one end thereof. The lug-containing end of the sleeve is located adjacent the plunger end 18 of the ampule body. The other end of the sleeve extends beyond the orifice end 20 of the ampule body and encapsulates the orifice means. Additionally, a portion of standoff 118 is surrounded by sleeve 138. Sleeve 138 is operable to retain end bushing 68 on ampule body 16 when the medication is dispensed under high pressure.

Sleeve 138 in the preferred embodiment has a pair of wasted areas 142 located along a length thereof and provides a view of the contents of the ampule therethrough. Ampule body 16 may include medication-volume indicia 144 thereon. The indicia and the waste areas are constructed and arranged to allow observation of indicia 144 through wasted areas 142. Sleeve 138 and standoff 118 comprise what is referred to herein as an ampule shroud.

Referring now to FIG. 2, ampule 12 is depicted in what is referred to herein as an initial condition. This is the condition in which the ampule would be received by the end-user patient. Medication 66 is sealed in medication holder 28 with one end of the holder being sealed by plunger 32 and the other end of holder 28 being sealed by floating seal 46.

To prepare the ampule for use, plunger 32 is manually shifted a distance along the path depicted by arrow 145. Due to the non-compressibility of the fluid medication 66, floating seal 46 is forced from the other end of holder 28 through transfer area 58 and into bypass area 60. O-ring 56 abuts an edge 63 of bypass area 60 while disc 50 abuts end bushing 68 thereby stopping movement of floating seal 46 toward orifice end 20. Pressure on plunger 32 is released when seal 46 contacts end bushing 68. Medication 66 is thus moved into transfer area 58. Plunger 32 is moved toward orifice end 20 until medication 66 completely fills transfer area 58. The ampule is now in what is described herein as a ready condition and is ready for joinder with device 14. During the injection, medication 66 moves through bypass area key ways 64, around seal 46, and through the orifice in a skin-piercing stream. After the injection has been given, the ampule is in a spent condition, which is depicted in FIG. 3.

Referring now to FIGS. 1, 7 and 8, device 14 will be described in greater detail. Device 14 includes a housing 200 which is an elongate, substantially hollow structure having an ampule-receiving chamber 202 at one end thereof and a pressure chamber 204 at the other end thereof. A partition 206 is located between the chambers and includes a gas-delivery passage 208 and a pressure release passage 210 extending therethrough. Pressure release passage 210 has a screw 212 therein which provides for slow release of pressure in ampule-receiving chamber 202 once the device has been fired. Alternately, screw 212 may have a very small diameter orifice therethrough.

A valve assembly, shown generally at 214, is located in pressure chamber 204. Valve assembly 214 includes a valve body 216 which has a cavity 218 therein. Cavity 218 includes a valve shaft-receiving portion 220 and a gas-passage portion 222. A gas transfer tube 224 extends from gas-passage portion 222 to gas-delivery passage 208, thereby connecting cavity 218 with ampule-receiving chamber 202 and maintaining a desired spacing between partition 206 and valve assembly 214.

A poppet valve 226 includes a valve head 228 and a valve shaft 230. Shaft 230 is received in valve-shaft receiving portion 220 and extends beyond the one end of valve body 216 through a valve-end retaining plate 232. Retaining plate 232 is held in place by a pair of opposed screws 234. An O-ring 236 is located on shaft 230 and provides a gas-tight seal thereabout.

Valve head 228 has an inner, sealing portion 238 and a formed cap 240 which surrounds sealing portion 238. Sealing portion 238 contacts a valve seat 242 on valve body 216. A coil spring 244 acts on cap 240 to maintain valve 226 in a sealed condition against valve seat 242. The other end of coil spring 244 presses against a valve end cap 246, which is secured to valve body 216 with a threaded joint 248.

End cap 246 includes a puncture pin 250 which is operable to pierce a frangible seal on the end of a gas-charge bearing cylinder 252. Cylinder 252 is received in pressure chamber 204 and is removable therefrom by virtue of a housing cap 254 which is threadably received on housing 200. A threaded shaft may be provided at the end of cap 254 to force the cylinder down on pin 250.

End cap 246 includes a compression seal 256 which provides a seal about a neck 252a of cylinder 252 to form a gas-tight seal thereabout. Valve assembly 214 is maintained in place in housing 200 by transfer tube 224 on one end of the assembly and by a split ring 258 which is located on the other end of the valve assembly.

An actuator mechanism 260 is operable to open poppet valve 226, thereby delivering a gas charge from cylinder 252 through the valve assembly into ampule-receiving chamber 202. Mechanism 260 includes a rocker-arm support 262 which is fixed on one end of valve body 216 and provides a pivoting support for a rocker arm 264. One end of the rocker arm is pivotably mounted on rocker-arm support 262 while the other end extends through a slot 266 in the side of housing 200. An actuator lever 268 is mounted on the free end of rocker arm 264 and extends along the exterior of housing 200. Assembly 260 is constructed such that when lever 268 is shifted toward housing 200, into a firing position, rocker arm 264 acts on poppet valve shaft 230, thereby opening poppet valve 226 and allowing passage of a gas charge from cylinder 252 into ampule-receiving chamber 202. Movement of gas into chamber 202 causes an ampule plunger-driving piston 270 to shift toward the free end of chamber 202, thereby acting on an ampule plunger received in the chamber. Piston 270, in the preferred embodiment, is a cylindrical, cap-like structure which includes a groove 272 about the periphery thereof and includes an O-ring 274 received in the groove.

Piston 270 is normally biased toward one end of chamber 202 by a spring 276. Spring 276 is of sufficient strength to return piston 270 to its ready position at the end of the chamber but does not provide sufficient resistance to decrease the force of piston 270 when a gas charge is caused to act upon it.

An injection-counting ring 278 is received in a groove 280 formed about housing 200 adjacent valve assembly 214. Referring now specifically to FIG. 9, ring 278 has alternating deep, or injection allowing, 282 and shallow, or injection prohibiting, 284 notches spaced evenly about the periphery thereof. The ring is constructed and arranged such that actuator lever 268 may not be moved to the firing position when received in a shallow notch 284 and may be moved to the firing position when received in a deep notch 282. A set screw 286 is received in ring 278 and includes a spring-biased dog 288 which acts with a series of detents 290 arranged about the periphery of groove 280. Dog 288 and detents 290 are constructed such that ring 278 may be rotated in only one direction about housing 200. A series of numbers, indicative of the number of injections which may be powered by a single cartridge, is provided about the periphery of ring 278. In the example shown in the preferred embodiment, cartridge 252 contains a gas charge which is sufficient to provide five injections of medication carried in five separate ampules, such as ampule 12. In this particular instance, ampule 12 contains 1.0 cc of medication. The patient using the assembly is taught to rotate ring 278 following each injection to a position where actuator lever 268 is received in a shallow notch. The ring must then be moved to a deep notch before the device may be used again. Appropriate notations are provided to indicate that a new cylinder must be inserted in pressure chamber 204 after a fifth injection is provided.

To use assembly 10 to administer an injection, device 14 is initially prepared by rotating ring 278 to a zero position with actuator lever 268 received in a shallow notch. A fresh cylinder 252 is installed in the recess in valve end cap 246 and housing cap 254 is installed and tightened on the housing. The action of tightening housing cap 254 causes a frangible seal in neck 252a of cylinder 252 to be punctured by puncture pin 250, thereby releasing a part of the gas charge in the cylinder into the first stage of the valve assembly.

An ampule containing a desired amount of the medication is prepared to the ready condition as previously described. An ampule sleeve 138 is then installed over the ampule body and the ampule installed on device 14 with plunger head 44 in contact with driving piston 270. The ampule and sleeve are secured to device 14 by means of the lug, or bayonet mount, which is provided by lugs 140 and grooves 136. Once the ampule and device are formed into the desired assembly, and ring 278 is rotated such that actuator lever 268 is over a deep groove, the assembly is brought into contact with the patient's skin, with standoff 118 contacting the skin. The actuator lever is then depressed, releasing a gas charge from the first stage of the valve assembly into the second stage, or ampule-receiving chamber, thereby moving piston 270 toward the free end of the chamber and in turn, depressing plunger 32 forcing the medication through needle 98 with sufficient velocity to form a skin-piercing injection stream which will extend below the level of the outer layer of the patient's skin to a desired depth.

Once the injection has been administered, ring 278 is rotated to a position such that a shallow notch is aligned with actuator lever 268 to prevent inadvertent firing of device 14. The ampule and sleeve are removed from the device. The ampule is discarded. Device 14 and sleeve 138 are then ready for the next injection. Once poppet valve 226 is allowed to close, by the release of actuator lever 268 and rocker arm 264, the gas charge will bleed out of chamber 202 around plug 212 and spring 276 will act on piston 270 to return the piston to its ready position at the interior end of ampule-receiving chamber 202.

Although a preferred embodiment of the assembly of the invention has been disclosed, it should be appreciated that variations and modifications may be made thereto without departing from the scope of the invention as defined in the appended claims.

It is claimed and desired to be secured by Letters Patent:

1. An ampule for non-invasive injecting of medication comprising:
   an elongate ampule body having a plunger end and an orifice end, a medication holder-retaining area adjacent to said plunger end and a transfer area adjacent to said orifice end;
   an elongate medication holder formed from a non-absorbing, non-diffusing, non-reacting material received in said medication holder-retaining area and having a free, plunger-receiving end located adjacent said body plunger end;
   a plunger having one end thereof received in and closing one end of said medication holder plunger-receiving end;
   a floating seal received in and closing the other end of said medication holder;
   orifice means for forming a skin-piercing injection stream located at one end of said transfer area;
   a bypass area located adjacent said one end of said transfer area, said bypass area being constructed and arranged to provide passage for medication from said transfer area to said orifice means with said floating seal positioned therein; and
   attachment means for securing said ampule to an injection device.

2. The assembly of claim 1 wherein said orifice means includes an ampule end bushing at least partially received in said transfer area, a needle orifice holder having a truncated hypodermic needle carried thereon, an orifice end cap received on said end bushing retaining said orifice holder thereon, and which further includes an orifice standoff constructed and arranged to prevent penetration of the skin of an injection-receiving patient by said needle.

3. The assembly of claim 2 wherein said end bushing includes a disc portion which abuts said orifice end of said body, a generally cylindrical medication receiving extension which extends from said disc portion into said transfer area, and an end cap-receiving extension for receiving said end cap thereon.

4. The assembly of claim 2 wherein said standoff is constructed and arranged to provide spacing between the end of said needle and the patient's skin by a predetermined distance.

5. The assembly of claim 4 wherein said attachment means includes an elongate ampule sleeve which extends about said ampule body along the length thereof, one end of said sleeve being located adjacent said medication holder-retaining area.

6. The assembly of claim 5 wherein said sleeve has lugs spaced about the periphery of one end thereof.

7. The assembly of claim 5 wherein said ampule body has medication-volume indicia thereon and said sleeve has at least one wasted area along a portion thereof for providing a viewing window for said indicia.

8. An ampule and a non-invasive hypodermic injection device assembly comprising:
   an injection device including a housing having an ampule-receiving chamber, a gas charge, and means for delivering a predetermined amount of gas to said ampule-receiving chamber; and
   a pre-filled ampule having a predetermined amount of medication therein, said ampule comprising:
   an elongate, ampule body having a plunger end and an orifice end, an elongate, medication holder-retaining area having one end thereof adjacent to said plunger end and the other end thereof located intermediate the ends of said body and an elongate transfer area having one end thereof located adjacent to said orifice end and the other end thereof located adjacent said medication holder-retaining area other end;
   an elongate medication holder formed from a non-absorbing, non-diffusing, non-reacting material received in said medication holder-retaining area and having a free, plunger-receiving end located co-terminally with said plunger end;
   a plunger having one end thereof received in and closing said plunger-receiving end, the other end thereof being received in said ampule-receiving chamber for action thereon by said gas charge;

a floating seal received in and closing the other end of said medication holder-retaining area;

orifice means for forming a skin-piercing injection stream located at one end of said transfer area including an ampule end bushing at least partially received in said transfer area, a needle orifice holder having a truncated hypodermic needle carried thereon, an orifice end cap received on said end bushing and retaining said orifice holder thereon, and which further includes a needle standoff constructed and arranged to prevent penetration of the skin of an injection-receiving patient by said needle;

a bypass area located adjacent said one end of said transfer area, said bypass area including key ways therein constructed and arranged to provide passage for medication from said transfer area to said orifice means with said floating seal positioned in said bypass area; and attachment means for securing said ampule to said device.

9. The assembly of claim 8 wherein said end cap has a generally cylindrical form of substantially the same diameter as said outer wall predetermined diameter along a first length thereof and a stepped-down diameter along a second length thereof, said end cap including a medication receiving portion extending from an end thereof into said medication retaining cavity, said medication receiving portion having a truncated conical bore therein with the wider end of said bore located in said medication retaining cavity.

10. The assembly of claim 9 wherein said standoff is constructed and arranged to provide spacing between the end of said needle and the patient's skin by a predetermined distance.

11. The assembly of claim 8 wherein said attachment means includes an elongate ampule sleeve which extends about said ampule body along the length thereof and a retainer collar on said device housing, one end of said sleeve being located adjacent said medication holder-retaining area and being retained on said device housing by said retainer collar, wherein said sleeve retains said orifice means and said standoff on said ampule body.

12. The assembly of claim 11 wherein said sleeve has lugs spaced about the periphery of one end thereof and wherein said collar has lug-receiving grooves therein.

13. The assembly of claim 12 wherein said ampule body has medication-volume indicia thereon and said sleeve has at least one wasted area along a portion thereof for providing a viewing window for said indicia.

14. The assembly of claim 8 wherein said device includes an elongate, hollow housing having said ampule-receiving chamber at one end thereof, a pressure chamber at the other end thereof and a partition located between said chambers, said partition having a gas-delivery passage extending therethrough;

said pressure chamber having said gas charge and a valve assembly therein, said valve assembly including a valve body having a cavity therein, said cavity including a valve-shaft receiving portion extending from one end of said body to the other end thereof and a gas-passage portion;

a valve end cap secured to the other end of said body having a recess for receiving an end of a gas-charge containing cartridge and a puncture pin located in said recess for piercing said cartridge received in said pressure chamber to release said gas charge;

a poppet valve having a valve head for closing the cavity on the other end of said valve body, a valve shaft received in said cavity and extending therethrough to said one end of said valve body;

a rocker-arm support fixed to said one end of said valve body, a rocker arm pivotably secured at one end thereof to said rocker-arm support with the other, free end, of said rocker arm extending through a slot in the side of said housing to the exterior thereof, and an elongate actuator lever secured to the free end of said rocker arm and extending along the exterior of said housing, said rocker arm and said rocker-arm support being constructed and arranged to provide shiftable contact between said poppet valve shaft and said rocker arm to shift said poppet valve to an open position with movement of said lever towards said housing;

a gas transfer tube extending between said gas-delivery passage and said valve body cavity for directing a gas charge to said ampule-receiving chamber when said poppet valve is opened;

an ampule plunger-driving piston shiftably located in said ampule-receiving chamber; and an ampule retaining collar located on said one end of said housing for securing an ampule to said housing, said collar having ampule sleeve bayonet-receiving grooves therein for receiving a bayonet lug on an ampule sleeve.

15. The assembly of claim 14 which further includes an injection-counting ring received in a groove extending about said housing, said ring having alternating injection allowing/prohibiting notches formed about the periphery thereof and including means to allow one-way only rotation of said ring relative to said housing.

* * * * *